(12) United States Patent
Gardner et al.

(10) Patent No.: US 8,454,224 B1
(45) Date of Patent: Jun. 4, 2013

(54) FOMITE TUMBLER AND METHOD OF TRANSFERRING BIOLOGICAL MATERIAL

(75) Inventors: Warren L. Gardner, Bel Air, MD (US);
Jerold R. Bottiger, Aberdeen, MD (US);
William R. Sayers, Joppa, MD (US);
Leslie I. Williams, Belcamp, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/955,307

(22) Filed: Nov. 29, 2010

Related U.S. Application Data

(60) Provisional application No. 61/264,999, filed on Nov. 30, 2009.

(51) Int. Cl.
*B01F 9/00* (2006.01)
*G01N 1/04* (2006.01)
*G01N 1/00* (2006.01)

(52) U.S. Cl.
USPC .................... 366/228; 73/864.71; 436/174

(58) Field of Classification Search
USPC .............. 73/864.1, 864.17; 366/228; 436/174
See application file for complete search history.

(56) References Cited

U.S. PATENT DOCUMENTS

| | | | |
|---|---|---|---|
| 2004/0045342 A1* | 3/2004 | Jones et al. | 73/37 |
| 2005/0229651 A1* | 10/2005 | Ahn | 68/139 |
| 2006/0260420 A1* | 11/2006 | Iguchi | 73/864.51 |

* cited by examiner

*Primary Examiner* — Michael Marcheschi
*Assistant Examiner* — Christopher Vandeusen
(74) *Attorney, Agent, or Firm* — Ulysses John Biffoni

(57) ABSTRACT

A fomite tumbler and method of transferring an agent from a source object to one or more fomites is provided. The tumbler provides reproducible and adjustable experimental determination of agent transfer between objects such as during handling. The inventions provide a unique mechanism for studying the transfer of a biological agent through a public use system such as the United States Postal System.

12 Claims, 3 Drawing Sheets

FIG. 2

FIG. 3

FOMITE TUMBLER AND METHOD OF TRANSFERRING BIOLOGICAL MATERIAL

CROSS-REFERENCE TO RELATED APPLICATIONS

This application claims priority to U.S. Patent Application No. 61/264,999 filed Nov. 30, 2009, the entire contents of which are incorporated herein by reference.

FIELD OF THE INVENTION

The invention relates to biological material transfer between fomites. More specifically, the invention relates to a device and method for reproducibly and quantitatively analyzing transfer of biological agents such as *Bacillus anthracis* spores from a source envelope to other envelopes. The device and methods provide insights into biological agent transmission during handling of contaminated objects.

BACKGROUND OF THE INVENTION

In September and October of 2001, letters containing *B. anthracis* spores were distributed through the U.S. Postal Service resulting in contamination of the mail processing and distribution center in Hamilton, N.J., as well as affiliated processing centers in Washington D.C., New York City and Wallingford, Conn., and postal facilities along the path transited by letters mailed to a targeted media company in Florida. Subsequently, 22 individuals including postal workers, persons who received or handled the contaminated letters, and persons exposed to environments contaminated by the letters developed cases of anthrax including both the inhalation and the cutaneous forms of the disease (5, 18-20). Five of these cases of anthrax resulted in death (4, 7).

Three cases were reported of individuals developing inhalation or cutaneous anthrax infection who were not associated with any of the known infected sites. The living and work environments of these individuals showed none or only a single environmentally positive sample. It was hypothesized that these individuals may have contracted the infectious agent through contaminated mail that picked up spores when contacting a source letter, or secondary letter.

These cases raise particular questions concerning the ability of disease-causing organisms to spread through cross contamination of second and even third generation fomites in sufficient numbers to cause infection and possible death. Unfortunately, studies of the primary fomites following attacks are difficult due to their use as evidence in a criminal investigation leaving little, if any, material available for study. In addition, the owners of the contaminated fomites have a desire to have their property returned in a non-contaminated and undamaged state to protect the personal and market value of the materials. Thus, there is a need for devices and methods useful for supporting non-destructive scientific evaluation of biological agent transfer between fomites such as mailing envelopes that can simulate field activities and provide valuable information to improve protection of the public.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A fomite tumbler is provided that includes a driver housing, a motor mechanically associated with the driver housing, a drum removably connected to the driver housing, and an insert removably connected to the drum optionally by one or more set screws. A plurality of fins are provided interior of the insert to aid in tumbling objects when the insert is rotated about an axis passing through the interior. The nested configuration of the housing, optional drum, and insert provide a common axis of rotation during operation of the tumbler. An insert optionally includes one or more holes traversing a first end of the insert. The tumbler is optionally supported by one or more supports rotatably attached to the housing.

A method of transferring agent between a source object and one or more fomites is also provided whereby a source object and at least one fomite is placed within a tumbler and the tumbler or portion thereof is rotated. Run time is optionally 1 hour or less with a rotational speed of at or between 1 to 5 rpm. The amount of agent transferred during a run onto each fomite is optionally quantified. A second or third stage is optionally performed whereby a fomite from a prior stage is used as a source object in a replicate run and the amount of agent transferred to second or third stage fomites is optionally quantified.

BRIEF DESCRIPTION OF THE DRAWINGS

FIG. 2 is a schematic of a multistage method for determining the transfer of agent from a source object to a fomite according to one embodiment of the invention;

FIG. 3 illustrates the tumbling time of *Bacillus atrophaeus* and level of transfer from a source object to a fomite;

DETAILED DESCRIPTION OF EMBODIMENTS OF THE INVENTION

Figure 1A:
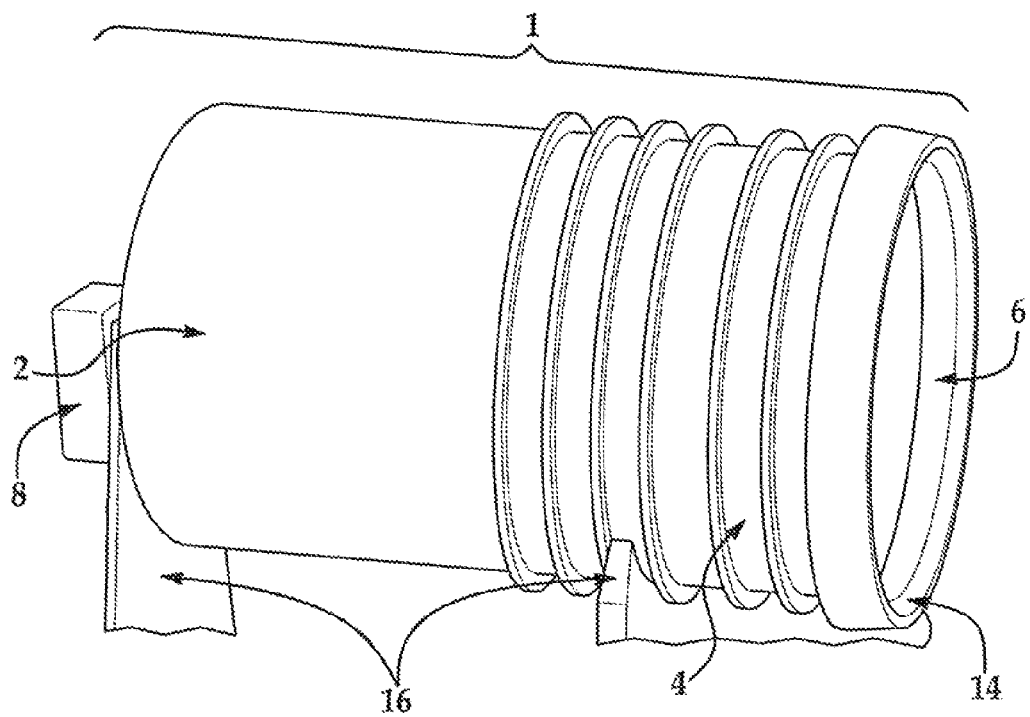
FIG. 1A is an external view of the fomite tumbler according to one embodiment of the invention.

The following description of particular embodiments of the invention is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The invention has utility as a scientific instrument to study transfer of biological agents between fomites. The description herein is directed to transfer of the biological agent *B. anthracis* spores, but it is appreciated that the devices and methods herein are equally applicable to study of the transfer of many other agents including biological agents, environmental agents, or other materials, compositions, or compounds. The identity of these other agents is readily appreciated by one of ordinary skill in the art, and these agents are encompassed within the scope of the invention.

An embodiment of a fomite tumbler according to the invention is illustrated in FIG. 1. A tumbler 1 includes a driver housing 2, a drum 4, an insert 6, and a motor 8. A housing 2 is illustratively a cylinder, but any other shape is operable. Illustratively, a housing 2 has a cross sectional area that is: circular, oval or other curvilinear shape; a square, pentagon, hexagon, or other polygon; or an irregular shape. A housing 2 has a first end that is open to accept at least a portion of a drum 4. A housing 2 also has a second end that is associated with a motor 8. The association between a motor 8 and a housing 2 is illustratively a direct association whereby a portion of a motor, illustratively a drive shaft, is physically connected to a portion of housing. Optionally an indirect association between a housing and a motor is present illustratively by in intermediate structure such as a belt, chain, or gearing. Other mechanisms of transferring rotational or other motion from a motor to a housing are similarly operable.

A housing 2 is made from a material with sufficient rigidity to transfer rotational motion to a drum. Illustrative examples include: polymers illustratively thermoplastics or thermoset plastics; glass; metals; other materials known in the art; or combinations thereof. In some embodiments, a housing is a plastic five gallon bucket.

A housing 2 is associated with a motor 8 at a second end. A motor is any motor type operable to produce rotational motion in the housing 2. A motor 8 is illustratively powered by electricity, gasoline, diesel, or other energy source. In general, the rotational force provided by a motor need only be sufficient to rotate a drum and associated chambers. Optionally, rotational speed is between 1 and 60 revolutions per minute (RPM). Rotational speed is optionally between 1 and 30 rpm, between 1 and 10 rpm, or between 1 and 5 rpm. In some embodiments rotational speed is 3 rpm.

A first end of a housing 2 is suitably dimensioned to accept at least a portion of a drum 4 or an insert 6. A drum 4 or insert 6 is optionally removably or fixedly associated with a housing 2 wherein at least a portion of a drum 4 or insert 6 fits within the interior of a housing 2. As depicted in FIG. 1A, a housing associates with a drum 4 positioned at least partially within the interior of the housing 2 and an insert 6 positioned within the drum 4. Thus, a tumbler optionally includes a drum 4 and an insert 6, or a drum is absent and an insert is directly associated with and inserted into a housing.

FIG. 1A depicts a housing 2 as a bucket whereby a drum 4 is inserted into the first end of the housing leaving a portion of the drum 4 exterior to the housing 2. In embodiments wherein a drum 4 is removable, sterilization of the drum 4 between experimental runs facilitates improved results with lower risk of contamination from agents present in a prior run.

A drum 4 is made from any material that is sterilizable. Illustratively, a drum is made from the same or different material as housing. It is appreciated that a drum is optionally autoclavable, or sterilizable by immersion in or wiping with antiseptic or sterilizing solution such as 10% bleach/water or 70% ethanol/water. A drum 4 has a first end that is open and a second end that is closed. The closed second end prevents contamination of the housing 2 with one or more agents during operation of a tumbler. The open first end allows a drum 4 to accept an insert 6.

An insert 6 is included as the chamber wherein an agent is experimentally transferred from a source object to one or more fomites. As such, an insert optionally houses or includes one or more source objects and/or one or more agents. A source object is any object with an agent on its surface or in its interior. A source object is illustratively an envelope. An insert 6 is dimensioned to fit within a drum 4 or directly in a housing 2. FIG. 1A depicts an embodiment where an insert 6 is positioned entirely within a drum 2. An insert 6 is made from the same or different materials as a housing 2 or a drum 4. In some embodiments, an insert 6 is made from stainless steel or other rust resistant and sterilizable material. An insert 6 has a cross sectional shape that is optionally the same or different from a housing 2 or a drum 4, with the appreciation that the cross sectional shape is complementary to that of a drum or a housing so that the insert can be contained therein and be fixedly associated with the drum or the housing.

An insert 6 is optionally fixedly associated with a drum 4 or housing 2 so that rotation of the housing 2 causes rotation of the insert 6. This association is optionally by a press fit, a latch, hook, or by one or more set screws in the wall of the insert that fixedly associate with the wall of a housing or drum. Between 1 and 5 set screws are optionally present.

Figure 1B:
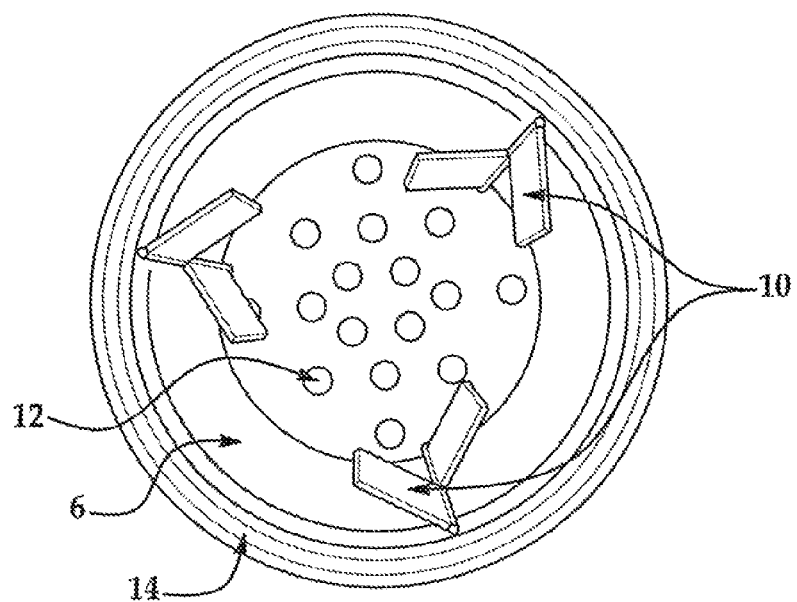
FIG. 1B is a view into the open end of the fomite tumbler according to one embodiment of the invention.

As depicted in FIG. 1B, an insert optionally includes one or more fins 10, optionally three fins, that serve to tumble one or more fomites within the insert during rotation. Fins 10 are optionally set within an insert 6 in alternating directions such as different angles relative to a rotational axis, different angles relative to a wall of the insert, or are of different sizes or shapes. Optionally, each of a plurality of fins is identical to the other fins or to a subset of other fins. A fin is optionally made from the same or different material as the remainder of the insert. A fin 10 is positioned along the wall of an insert with an edge abutting the wall and protruding into the interior of the insert 6. A fin optionally includes a grating, dimples, or other shape or space to facilitate fomite tumbling and resist adherence of a fomite to the fin during operation. A fin 10 is optionally polished, rounded, or otherwise shaped to eliminate sharp edges. A sharp edge is an edge suitably acute to tear or otherwise compromise a fomite during operation of the tumbler, or to compromise safety equipment of a user.

An insert 6 optionally includes one or more holes 12 traversing a second end. A second end is an end of an insert 6 that is positioned nearest the housing or motor and opposite the open end of the insert 6. The presence of one or more holes 12 allows airflow through the insert when it is being positioned in the interior of a drum 4 or housing 2 reducing the likelihood of moving any agents during insertion such as spores in the drum 4 or insert 6. Optionally, a plurality of holes is present on the second end of the drum. In some embodiments, a single hole is sufficient to provide the needed ease of insertion and safety.

A ring 14 is optionally included on the first end of a drum 4 or a housing 2. The ring 14 may be press fitted or otherwise fixedly associated with the rim or interior wall of the drum 4 or housing 2. A ring is optionally threaded to associate with a lid. When a tumbler is operated, a lid encloses a tumbling chamber within the interior of an insert preventing aerosolization of the agent being tumbled. This improves the safety of operation particularly with biohazard 2 through 4 agents.

One or more blocks 16 are optionally associated with a housing 2 and/or a motor 8 that provide support for the housing, drum, insert, motor, and other components of a tumbler. A block is optionally rotatably associated with a housing so that friction from the rotation of the housing is minimized. Examples of blocks that allow rotation include low friction material blocks, are illustratively made of a material such as polytetrafluoroethylene (PTFE) sold as TEFLON, or other low friction material. Optionally, a low friction material tape or other veneer is applied to a contact surface of one or more blocks. In some embodiments, one or more bearings are included on the contact surface of one or more blocks that allow low friction rotation of the housing.

Also provided is a method of determining or detecting transfer of an agent from a source object to a fomite. A method includes providing a tumbler such as that described herein, inserting a source object and at least one first fomite into the interior of the tumbler and rotating the tumbler to agitate the relative positions of the source object and the first fomite. A tumbler is optionally rotated anywhere from 1 to 60 rpm, optionally 1 to 5 rpm, optionally 3 rpm. Rotational speed is optionally constant throughout the run or may vary according to the protocol used. Rotation of the housing is optionally in a single direction or, optionally, alternates direction once or a plurality of times during a run.

During a run, defined as the time of rotation, a fomite is agitated with respect to a source object or other fomite. A run is optionally from 1 minute to 5 hours. The inventors discovered that a run time of 1 hour is sufficient to cause full transfer of B. arthracis spores between a source object and a fomite. Appreciable additional transfer for longer run times is not observed. As such, a run is optionally one hour. A run may additionally include a rest period at the end of the rotational time. A rest period is illustratively one hour or less, optionally 30 minutes.

After a run, the amount of agent present on a fomite, a source object, the tumbler or any subpart therebetween is quantified. Techniques of quantification vary depending on the type of agent being studied. Illustrative examples of quantification techniques include PCR based techniques such as PCR, RT-PCR, or other method of detecting oligonucleotides, culturing, mass spectrometry, immunoassay, or other technique known in the art. Examples of these and other techniques are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992; the contents of each of which are incorporated herein by reference.

A method of transferring agent optionally includes a second stage whereby one or more first fomites are transferred from a tumbler to a second tumbler to act as a second source object. One or more second fomites are then added to the second tumbler and a run is performed by rotating the second tumbler. The amount of agent transferred to a second fomite is optionally determined by quantifying the amount of agent remaining on the first fomite, on the tumbler or subportion thereof, or directly present on the second fomite following the run. It is appreciated that a second tumbler may be the same as the first tumbler whereby the insert and optional drum are sterilized prior to the second run.

A third, fourth, or additional stages are optionally included whereby a fomite from a prior stage is used as a source object for transfer to additional fomites in subsequent stages. This allows a user to determine how additional handling affects agent transfer. The parameters of run time, rest period time, rotational speed, number of rotational direction changes, etc. are optionally consistent or vary between a first or subsequent stage.

Various aspects of the present invention are illustrated by the following non-limiting examples. The examples are for illustrative purposes and are not a limitation on any practice of the present invention. It will be understood that variations and modifications can be made without departing from the spirit and scope of the invention.

Example 1

Determination of B. Anthracis Spore Transfer

Bacillus atrophaeus subsp. globigii Dugway Milled BG-Ml, lot #19076-03268, batch #40 spores (BG) are obtained from Dugway Proving Grounds (U.S. Army) and are used. Spores are milled to a median aerodynamic diameter of 1.30 µm and mean aerodynamic diameter of 1.66 µm. Spores are prepared as previously described in Brown et al., J. Appl. Microbiol., 2007, 103:1074-80. There are approximately $1 \times 10^{12}$ CFUs g$^{-1}$ in the material used to subsequent analyses.

A source object is created using one standard sized 10.4775 cm×24.13 cm (No. 10 business size) envelope stuffed with one 21.59 cm×27.94 cm (letter size) tri-folded piece of plain white printer paper containing one gram of the dry BG milled spores. The envelope is then sealed using a moistened cotton swab (Puritan; Fisher Scientific, Swanee, Ga.; catalog no. 14-959-102).

One 19 L drum with a 30.5 cm gamma seal lid (Pleasant Hill Grain, Aurora, Nebr.) is placed inside a tumbler housing. With the lid off, a sterile stainless steel insert is placed inside the bucket and secured by screwing three set screws toward the wall of the drum. Twenty-four 10.4775 cm×24.13 cm (No. 10 business size) envelopes (fomites) are stuffed with one sheet of 21.59 cm×27.94 cm (letter size) tri-folded white printer paper (non-agent coated) and sealed using a moistened cotton swab. Each fomite is numbered sequentially with pencil in the center and corners. The fomites are placed inside the stainless steel insert. One source object is placed inside the insert and on top of the 24 fomites. Five 0.47 mm glass fiber filters (Pall Life Sciences, VWR, West Chester, Pa.) are then placed on top of the source object. The lid is secured tightly and the drum is rotated for one hour at 3 rpm. After rotation time is complete, the tumbler is allowed to rest for 30 minutes. The fomites and source object are then removed individually with their order and orientation recorded. The first two envelopes, excluding the top envelope or the envelopes located immediately above and below the source object are selected and set aside for use in a second stage run.

The quantification samples consisting of the remaining envelopes and glass fiber filters are placed into individual a stomacher bags (Seward BA6141, West Sussex, UK) containing 35 mL of sterile deionized water and sealed. Each sample is mixed by a stomacher (Seward Circulator 400, West Sussex, UK) for two minutes at 260 rpm. The remaining liquid not absorbed by the envelope is removed using a sterile pipette, its volume recorded, and is placed into a 50 cc snap-cap conical tube (NUNC, Thermo Fisher Scientific, Rochester, N.Y.). Each sample is then diluted to extinction with 50 µL of deionized H2O plated on tryptic soy agar (TSA, Becton Dickenson, Sparks, Md.) in triplicate using a spiral plater (Spiral Biotech, Norwood, Mass.). Colonies are counted and CFU counts are stored electronically by Q-count (Spiral Biotech, Norwood, Mass.) with the final spore number calculated (Total CFU) for both controls and samples.

Primary tumbling of a source object with one gram of BG spores at $1 \times 10^{12}$ CFUs g$^{-1}$ produce a mean cross contamination of $9.18 \times 10^7$ CFUs per envelope and reduce the number of CFUs contained within and on the payload envelope to $1.08 \times 10^{10}$ CFUs. (Table 1) After the primary tumbling, $2.75 \times 10^8$ CFUs are recovered from the glass fiber filters. (Table 1.)

TABLE 1

|  | Primary Tumbling CFUs (CV %) n |
|---|---|
| Load Envelope | 1.01E+10 |
| Stuffed envelopes | 2.72E+08 (22%) n = 66 |
| Glass Fiber Filters | 5.88E+08 (45%) n = 15 |

Example 2

Second and Third Stage Agent Transfer

The insert and drum from the tumbler used in Example 1 are removed and subjected to autoclaving to sterilize them for subsequent use. Alternatively, a new 19 L drum with gamma seal lid is placed inside the housing, along with a sterile stainless steel insert. One envelope set aside from the primary or secondary run for use as a second stage source object is placed on top of 24 stuffed and sealed envelopes (second fomites) labeled sequentially as described in Example 1. A second stage run is performed identical to the procedure of Example 1. Five additional glass fiber filters are placed on top of the second stage source object. The gamma seal lid is secured tightly and the envelopes are tumbled for one hour at 3 rpm. The envelopes are allowed to rest for 30 minutes before processing. Two envelopes are set aside from the secondary stage to use as a third stage source object for tertiary contamination study using the same run parameters. All remaining envelopes from all runs are recorded and processed in the same manner as in Example 1. Two runs of each stage (primary, secondary, and tertiary) are performed in this manner.

After the second stage run, the first stage fomites contain $4.54 \times 10^7$ CFUs. These letters produce an average cross contamination of $9.3 \times 10^5$ CFUs per envelope. The envelopes that are cross contaminated in the tertiary tumbling are coated with $1.73 \times 10^4$ CFUs on average. The letters providing the source of contamination retained $2.31 \times 10^5$ CFUs (Table 2).

The secondary tumbling results in glass fiber filters retaining $6.73 \times 10^5$ CFUs while $2.37 \times 10^4$ CFUs are recovered from the glass fiber filters tumbled in the third stage run (Table 1).

TABLE 2

|  | Secondary Tumbling CFUs (CV %) n | Tertiary Tumbling CFUs (CV %) n |
|---|---|---|
| Load Envelope | 5.09E+07 | 2.33E+05 |
| Stuffed envelopes | 9.40E+05 (57%) n = 138 | 1.73E+04 (60%) n = 144 |
| Glass Fiber Filters | 6.73E+05 (43%) n = 30 | 2.43E+04 (46%) n = 30 |

Example 3

Surrogate Transfer Study: Contamination Distribution Over Time

Using the method of Examples 1 and 2 for a 1 g agent payload source object, the tumbler device is loaded with 24 stuffed and sealed marked envelopes (as described above) and 5 glass fiber filters, and tumbled for pre-determined time-points of 15 minutes, 30 minutes, two hours, four hours, or eight hours. The tumbler is then turned off, and the envelopes are allowed to sit at rest for 30 minutes. As in the contamination experiments of Examples 1 and 2, 10 of the 24 envelopes excluding the top envelope or the envelopes immediately above and below the source object, are selected for quantification. This procedure is repeated in triplicate for each of the five time points.

Figures 2, 3:
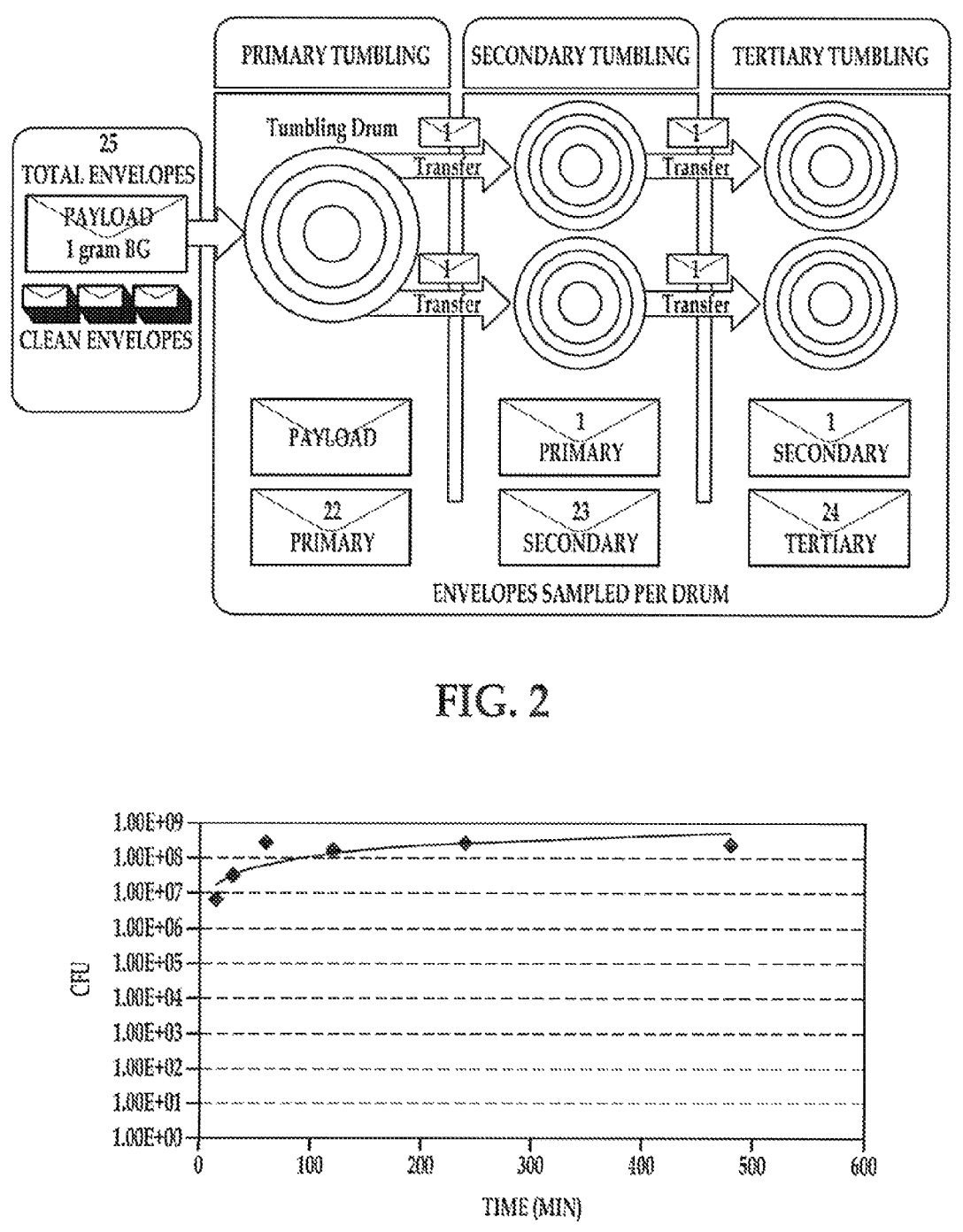

As illustrated in FIG. 3, at the 15 minute time point, cross contamination levels average $6.30 \times 10^6$ CFUs per envelope. After 30 minutes of tumbling an average of $3.08 \times 10^7$ CFUs/envelope is measured. After one hour of tumbling, an average cross contamination level of $2.72 \times 10^8$ CFUs/envelope is measured. The cross contamination levels plateau after one hour. Additional tumbling for two, four, and eight hours produce average spore levels of $1.59 \times 10^8$, $2.67 \times 10^8$, and $2.40 \times 10^8$ CFUs/envelope respectively (FIG. 3). These results indicate that a run time of 1 hour is sufficient to produce full transfer of *B. atrophaeus* spores from a source object to other fomites using a tumbler.

Example 6

Transfer of *B. Anthracis* Spores

Figure 4:
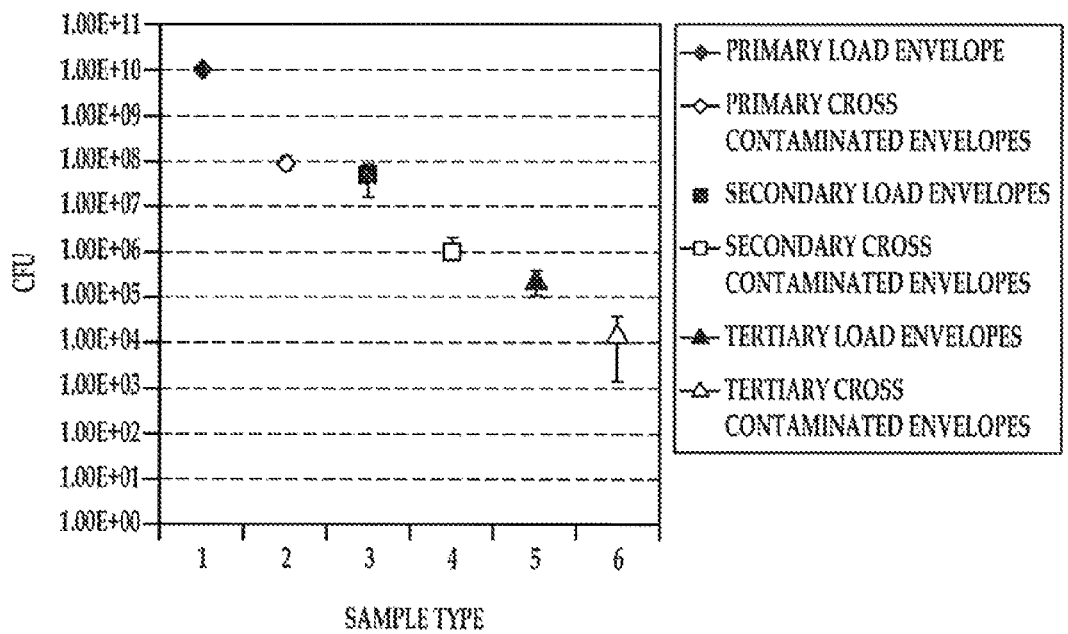
FIG. 4 illustrates the transfer levels of *Bacillus anthracis* between objects using one embodiment of the inventive tumbler.

The protocols of Examples 1-3 are repeated using spores from *B. anthracis* as source agent with the exception that the second and third stage runs are performed in duplicate. As seen in Table 3, after a first stage run the amount of spores transferred to fomites is nearly two logs less than the source object. This level continues nearly consistently in the second and third stage runs. These data are depicted graphically in FIG. 4.

TABLE 3

|  | Primary | Secondary A | Secondary B | Tertiary A | Tertiary B |
|---|---|---|---|---|---|
| Load Envelope | 1.21E+10 | 7.08E+07 | 6.41E+07 | 1.21E+05 | 6.57E+04 |
| Envelopes | 6.33E+08 | 1.41E+06 | 7.18E+05 | 1.54E+04 | 3.69E+03 |

The average data from three replicates of each run are illustrated in Table 4 illustrating tight correlation and high reproducibility.

TABLE 4

|  | Primary Tumbling | Secondary Tumbling | Tertiary Tumbling |
|---|---|---|---|
| Load Envelope | 1.08E+10 | 4.54E+07 | 2.31E+05 |
| Secondary Transfer Envelopes | 9.18E+07 | 9.30E+05 | 1.73E+04 |

Figure 5:
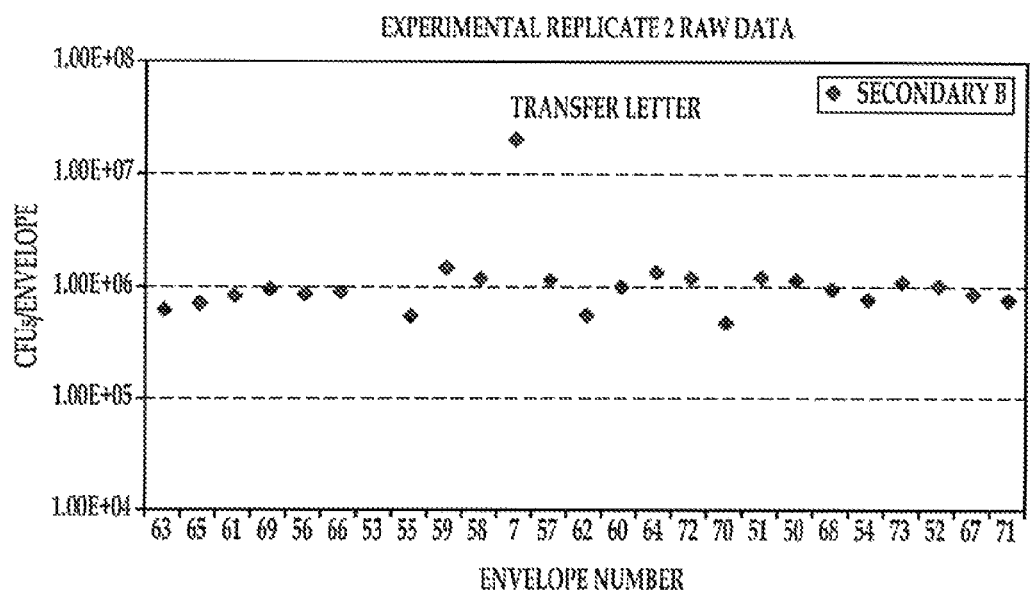
FIG. 5 illustrates the consistent level of transfer to a plurality of fomites from a source object during a single run using one embodiment of an inventive tumbler.

The reproducibility of transfer from a source object to 24 fomites is depicted in FIG. 5. The source object (envelope 7) shows increased spore levels relative to the fomites. The fomites, however, demonstrate high consistency in the amount of transferred material.

Examples 7-25

The protocols of Examples 1-3 are repeated with spores from *Bacillus cereus, Bacillus clausii, Bacillus halodenitrificans, Clostridium botulinum, Clostridium Clostridium perfringens, Clostridium tetani, Clostridium sordellii, Sporolactobacillus dextrus, Sporolactobacillus inulinus, Sporolactobacillus laevis, Sporolactobacillus terrae, Sporolactobacillus vineae, Sporosarcina aquimarina, Sporosarcina globispora, Sporosarcina halophila, Sporosarcina*

*koreensis, Sporosarcina luteola*, and *Sporosarcina ureae*. Similar results to those of *B. atrophaeus* and *B. anthracis* are observed.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

The foregoing description is illustrative of particular embodiments of the invention, but is not meant to be a limitation upon the practice thereof. The following claims, including all equivalents thereof, are intended to define the scope of the invention.

The invention claimed is:

1. A process of transferring an agent between a source object and a sealed mailing envelope, comprising:
   inserting a source object having an agent on its surface or in its interior and at least one sealed mailing envelope into a first tumbler;
   rotating said tumbler to cause the transfer of at least some of the agent from the source object to the sealed mailing envelope;
   removing a first sealed mailing envelope from said tumbler; and
   combining said first sealed mailing envelope with at least one second sealed mailing envelope in a second tumbler; and
   rotating said second tumbler to cause the transfer of at least some of the agent from the first sealed mailing envelope to the second sealed mailing envelope.

2. The process of claim 1, wherein said first and/or second tumbler is rotated for one hour or less.

3. The process of claim 1, wherein said first and/or second tumbler is rotated at between 1 and 5 revolutions per minute.

4. The process of claim 1, further comprising quantifying the amount of agent on said first sealed mailing envelope following said rotating of said first tumbler.

5. The process of claim 1, further comprising quantifying the amount of agent on said second sealed mailing envelope following said rotating of said second tumbler.

6. The process of claim 1, wherein said first and/second tumbler comprises:
   a driver housing;
   a motor mechanically associated with said driver housing; and
   an insert with an interior, said insert directly or indirectly, and removably connected to said housing.

7. The process of claim 6, wherein said first and/or second tumbler further comprises a drum removably connected to said housing with at least a portion of said drum positioned interior to said housing wherein said insert is indirectly connected to said housing via said drum.

8. The process of claim 6, wherein said insert further comprises a plurality of fins positioned within the interior of said insert.

9. The process of claim 6, wherein said insert further includes at least one set screw connecting said insert and said drum.

10. The process of claim 7, wherein said housing, drum, and insert share a common axis of rotation.

11. The process of claim 6, wherein said insert further comprises at least one hole within a first end interior to said drum.

12. The process of claim 6, wherein said first and/or second tumbler further comprises a support rotatably attached to said driver housing.

* * * * *